United States Patent
Zarychta et al.

(10) Patent No.: US 6,259,938 B1
(45) Date of Patent: Jul. 10, 2001

(54) MONITORING CATHETER AND METHOD OF USING SAME

(75) Inventors: Jaroslaw Zarychta, Winnipeg (CA); Eugene N. Scarberry, Trafford; Mark H. Sanders, Wexford, both of PA (US); Gregory L. Walker; Mark F. Sauerburger, both of Indianapolis, IN (US)

(73) Assignee: Respironics, Inc., Pittsburgh, PA (US)

( * ) Notice: Subject to any disclaimer, the term of this patent is extended or adjusted under 35 U.S.C. 154(b) by 0 days.

(21) Appl. No.: 09/312,540

(22) Filed: May 13, 1999

Related U.S. Application Data

(60) Provisional application No. 60/085,662, filed on May 15, 1998.

(51) Int. Cl.$^7$ ..................................................... A61S 5/04
(52) U.S. Cl. ...................... 600/380; 600/585; 600/546; 600/593; 604/528
(58) Field of Search ................................ 600/373–386, 600/585, 596, 547, 648, 561, 593; 607/122, 101; 604/528

(56) References Cited

U.S. PATENT DOCUMENTS

| | | |
|---|---|---|
| 3,608,543 | 9/1971 | Longini et al. . |
| 4,155,353 | 5/1979 | Rea et al. . |
| 4,182,342 | 1/1980 | Smith . |

(List continued on next page.)

OTHER PUBLICATIONS

Kimura, et al., "Determination of the Optimal Pressure Support Level Evaluated by Measuring Transdiaphragmatic Pressure", Chest, vol. 100, Jul., 1991, pp. 112–117.

Lorenco, "Diaphragm Activity in Obesity", The Journal of Clinical Investigation, vol. 48, Oct., 1968, pp. 1609–1614.

Bellemare et al., "Effect of Pressure and Timing of Contraction on Human Diaphragm Fatigue", The American Physiological Society, vol. 82, Jun., 1982, pp. 1190–1195.

Bellemare et al., "Evaluation of Human Diaphragm Fatigue", The American Physiological Society, vol. 82, Jun., 1982, pp. 1196–1206.

Laporta et al., "Assessment of Transdiaphragmatic Pressure in Humans", The Americal Physiological Society, vol. 85, Dec., 1984, pp. 1469–1476.

Lopata et al., "Respiratory Muscle Function during C02 Rebreathing with Inspiratory Flow–Resistive Loading", The Americal Physiological Society, vol. 83, Sep., 1982, pp. 475–482.

Onal et al., "Diaphragmatic and Genioglossal Electromyogram Responses to C02 Rebreathing in Humans", The Americal Physiological Society, vol. 81, Dec., 1980, pp. 1052–1055.

(List continued on next page.)

*Primary Examiner*—Linda C. M. Dvorak
*Assistant Examiner*—David M. Ruddy
(74) *Attorney, Agent, or Firm*—Michael W. Haas

(57) ABSTRACT

A monitoring catheter that inserts into the patient's esophagus alone or in combination with an existing catheter, such as a feeding or aspiration tube. The monitoring catheter includes a pair of EMG electrodes on an exposed surface that contact the patient's esophageal wall to measure the activity of the diaphragm and/or a pair of pressure detecting mechanisms that measure the pressures within the patient at separate locations. The electrodes are sized and spaced from one another so as to maximize detection of diaphragm muscle activity while minimizing detection of noise. The pressure detecting mechanisms are sized and spaced apart to measure the patient's esophageal and gastric pressures, for example. If necessary, an attaching mechanism secures at least a portion of the monitoring catheter to the existing catheter so that the monitoring catheter uses the existing catheter as a tracking guide.

7 Claims, 9 Drawing Sheets-

U.S. PATENT DOCUMENTS

| | | |
|---|---|---|
| 4,214,593 | 7/1980 | Imbruce et al. . |
| 4,248,240 | 2/1981 | van Eykern . |
| 4,270,542 | 6/1981 | Plumley . |
| 4,369,789 | 1/1983 | LeVeen et al. . |
| 4,485,805 | 12/1984 | Foster, Jr. . |
| 4,634,435 | 1/1987 | Ingraham . |
| 4,874,365 | 10/1989 | Frederick et al. . |
| 4,964,411 | 10/1990 | Johnson et al. . |
| 5,012,820 | 5/1991 | Meyer . |
| 5,058,602 | 10/1991 | Brody . |
| 5,109,870 | 5/1992 | Silny et al. . |
| 5,174,287 | 12/1992 | Kallok et al. . |
| 5,181,517 | 1/1993 | Hickey . |
| 5,199,433 | 4/1993 | Metzger et al. . |
| 5,263,485 | 11/1993 | Hickey . |
| 5,277,197 | 1/1994 | Church et al. . |
| 5,318,039 | 6/1994 | Kadefors et al. . |
| 5,318,527 | 6/1994 | Hyde et al. . |
| 5,370,679 | 12/1994 | Atlee, III . |
| 5,573,007 | 11/1996 | Bobo, Sr. . |
| 5,645,073 | 7/1997 | Kadefors et al. . |
| 5,662,606 | 9/1997 | Cimino et al. . |
| 5,671,752 | 9/1997 | Sinderby et al. . |
| 5,713,943 | 2/1998 | Lindegren . |
| 5,820,560 * | 10/1998 | Sinderby et al. ............ 600/546 |
| 5,902,331 * | 5/1999 | Bonner et al. ............ 607/122 |
| 6,063,022 * | 5/2000 | Ben-Haim ............ 600/41 |
| 6,096,036 * | 8/2000 | Bowe et al. ............ 606/41 |
| 6,120,442 * | 9/2000 | Hickey ............ 600/300 |

OTHER PUBLICATIONS

Lopata et al., "Diaphragmatic EMG and Occlusion Pressure Response to Elastic Loading during C02 Rebreathing in Humans", The Americal Physiological Society, vol. 80, May, 1980, pp. 669–675.

Onal et al., "Effects of Electrode Position onEsophageal Diaphragmatic EMG in Humans", The Americal Physiological Society, vol. 79, Jul., 1979, pp. 1234–1238.

Lopata et al., "Quantification of Diaphragmatic EMG Response to C02 Rebreathing in Humans", Journal of Applied Physiology, vol. 43, No. 2, Apr. 1976, pp. 262–270.

Carlson et al., "Acoustically Induced Cortical Arousal Increases Phasic Pharyngeal Muscle and Diaphragmatic EMG in NREM Sleep", The Americal Physiological Society, vol. 94, Nov., 1993, pp. 1553–1559.

Alex et al., "Effects of Continuous Positive Airway Pressure on Upper Airway and Respiratory Muscle Activity", The Americal Physiological Society, vol. 87, Dec., 1986, pp. 2026–2030.

Gross et al., "Electromyogram Pattern of Diaphragmatic Fatigue", The Americal Physiological Society, vol. 79, The Americal Physiological Society, vol. 79, Jul., 1978, pp. 1–7.

Schweitzer et al., "Spectral Analysis of Human Inspiratory Diaphragmatic Electromyograms", Journal of Applied Physiology, vol. 46, No. 1, Aug. 1978, pp. 152–165.

Moriette et al., "The Effect of Rebreathing C02 on Ventilation and Diaphragmatic Electromyography in Newborn Infants", Respiration Physiology, vol. 62, Aug. 1985, pp. 387–397.

* cited by examiner

MONITORING CATHETER AND METHOD OF USING SAME

This application claims the benefit of Provisional No. 60/085,662 filed May 15, 1998.

BACKGROUND OF THE INVENTION

1. Field of the Invention

The present invention pertains to a catheter that inserts into a patient's esophagus to measure physiological characteristics of the patient, and, in particular, to a monitoring catheter that, once inserted, measures the activity of the patient's diaphragm and/or measures pressures within the patient at multiple locations. The present invention also pertains to a method of using such a catheter to measure these physiological characteristics.

2. Description of the Related Art

There are many instances where it is important to determine a patient's diaphragmatic function and/or inspiratory effort. For example, it is not uncommon for a patient in an intensive care unit ("ICU") to have a breathing disorder that causes the patient to go into ventilatory failure and/or to have difficulty weaning from a mechanical ventilator. It is typically difficult to predict clinical deterioration or diagnose the cause of such a breathing disorder to optimize the settings on the ventilatory assist device or to determine a propitious time to initiate attempts to wean the patient from the mechanical ventilator. For example, the physician must determine whether the patient is failing to spontaneously ventilate properly due to muscle weakness or whether failure to properly ventilate is due to a dysfunctional central nervous system. If, for example, the patient's failure to properly ventilate is due to muscle weakness, the physician can then focus on determining the cause of the weakness, e.g., whether the weakness is the result of malnutrition, myopathy, drug effects, etc. Furthermore, from time to time, a patient may not ventilate adequately despite being treated with mechanical ventilation. This may have one or more of a number of causes. For example, there may be intrinsic positive end exhalation pressure (PEEP) or other patient-ventilator disharmony which, if identified, may be addressed.

Conventional patient monitoring devices are incapable of easily measuring the physiological conditions of the patient needed to access the diaphragmatic function and/or inspiratory effort of the patient. For example, the conventional technique for measuring esophageal pressure is to provide a catheter in the patient's esophagus. One conventional catheter has a plurality of pressure ports at its distal end with a balloon surrounding the ports. The balloon is inflated with about 0.5 cc of air to prevent blockage of the ports. The pressure ports are connected to a common lumen so that the catheter measures the pressure at one location within the patient. Such a device approximates the intrapleural pressure by detecting respiratory pressure swings while minimizing the detection of pressure caused by cardiac activity.

This conventional device is disadvantageous in that it only measures the pressure at one location in the patient, for example, at the distal end of the catheter. Measuring multiple pressures requires multiple pressure measuring catheters. In addition, conventional pressure measurement catheters require a separate insertion procedure, apart from the procedure required to insert a feeding tube in the patient. This separate insertion procedure exposes the patient to the additional risk that the conventional pressure sensor will be unintentionally inserted into the trachea tube.

It is also known that one way to measure diaphragm muscle activity using an electromyogram ("EMG") is to place electrodes on the surface of the patient's abdomen proximate to the diaphragm. Because the major portion of the diaphgram muscle is deep within the patient's abdomen, these external EMG electrodes are often not well suited to detect diaphragm EMG signals or are contaminated by signals from the muscles overlying the abdomen, as well as the cardiac activity of the patient. An article by Onal et al., entitled "Effects of Electrode Position on Esophageal Diaphragmatic EMG in Humans," published in volume 47, no. 9, pages 1234–8 of the Journal of Applied Physiology in December 1979 teaches that it is known to use an esphogeal catheter with multible electrodes disposed on an exterior surface to measure EMG activity. However, a suitable monitoring device using such internal EMG measurment techniques has not gained popular acceptance.

SUMMARY OF THE INVENTION

Accordingly, it is an object of the present invention to provide a patient monitoring device that overcomes the shortcomings of conventional physiological monitoring devices and techniques. This object is achieved according to one embodiment of the present invention by providing a monitoring catheter that places the EMG electrodes closer to the major portion of the diaphragm than conventional surface EMG devices. The catheter of this embodiment includes a first electrode disposed on a first portion of a body member of the catheter and a second electrode disposed on a second portion of the body member. First and second leads disposed within the catheter body are coupled, respectively, to the first and second electrodes. The first and second electrodes are sized and spaced apart on the catheter to maximize the detection of diaphragm EMG signals while minimizing noise from other sources, such as cardiac activity, when the catheter is properly positioned within the patient. Because the electrodes are located within the patient and in contact with the esophageal wall, they provide less noisy signals than convention external diaphragm EMG sensors. Furthermore, because the electrodes are sized, configured, and spaced apart on the catheter to maximize the detection of diaphragm EMG signals while minimizing noise, the monitoring catheter represents a significant improvement over conventional esophageal EMG catheters.

It is yet another object of the present invention to provide a unitary device that measures pressures within the patient at a plurality of locations, such as the patient's esophageal and gastric pressures. This object is achieved by providing a monitoring catheter that includes a body member having a first pressure detecting mechanism disposed at a first portion of the body member and a second pressure detecting mechanism disposed at a second portion of the body member. The first and second pressure detecting mechanisms are spaced apart from one another along the length of the body member. In an exemplary embodiment of the present invention, the body member includes a plurality of lumens that extend from a proximal end of the body member through at least a portion of the body member along a length thereof, and the first and second pressure detecting mechanisms are first and second pressure ports defined in first and second portions of the body member spaced apart from one another and operatively coupled to first and second lumens, respectively, in the plurality of lumens.

It is another object of the present invention to provide a patient monitoring catheter that performs one or both of the functions identified in the preceding paragraphs and that can be used in conjunction with a second catheter that is already placed within the patient. This object is achieved by providing a monitoring catheter that includes a pair of electrodes and/or a pair of pressure detecting mechanisms and an attaching mechanism associated with the monitoring catheter, wherein the attaching mechanism releaseably secures at least a portion of the body member of the monitoring catheter to the second catheter. In one embodiment of the present invention, the body member is releaseably secured to the second catheter by means of a guide loop formed from wrapping a guide line around the second catheter and attaching both ends of the guide line to the monitoring catheter. More specifically, one portion of the guide line is coupled to the body member and another portion is coupled to a securing member that selectively secures to a distal end portion of the body member, thereby capturing the second catheter via the guide loop. In another embodiment, the body member of the monitoring catheter includes a cavity defined in at least a portion thereof. The cavity is sized and structured such that the second catheter can be removeably positioned within this cavity, thereby attaching the second catheter to the monitoring catheter.

It is yet another object of the present invention to provide a method of measuring a physiological condition of a patient comprising the steps of introducing a catheter having a first pressure detecting mechanism and second pressure detecting mechanism into an esophagus of the patient; positioning the catheter within the patient such that a first pressure detecting mechanism is disposed at a first location within the patient and such that the second pressure detecting mechanism is disposed at a second location within the patient; and measuring the internal pressures at the first and second locations.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

Figure 1A:
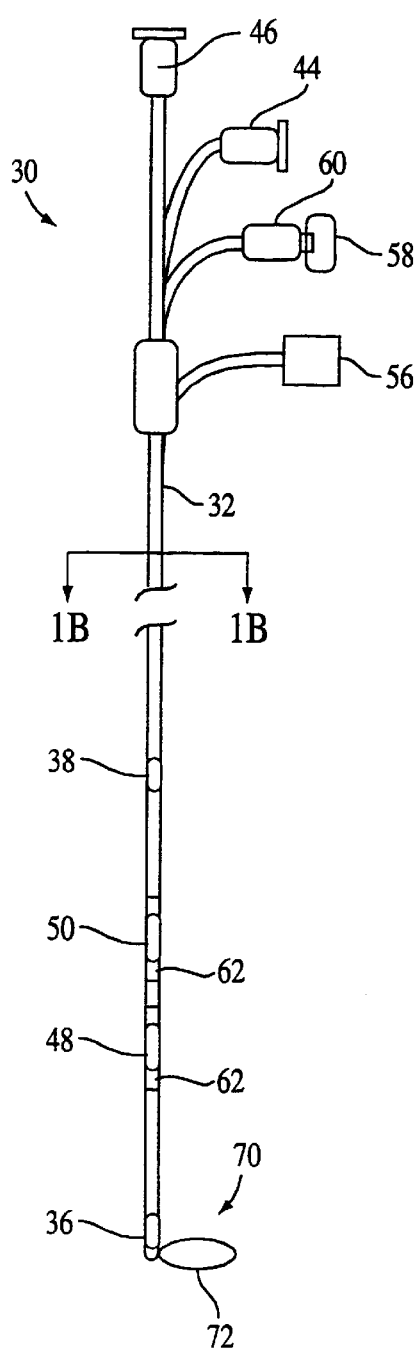
FIG. 1A is a side view of a first embodiment of a monitoring catheter according to the principles of the present invention.
Figure 1B:
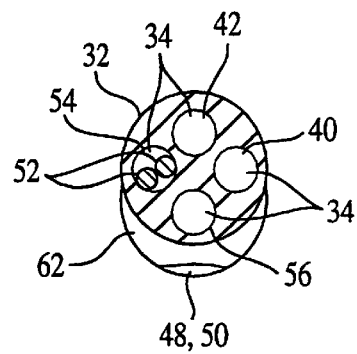
FIG. 1B is a cross-sectional view of the monitoring catheter taken along line 1B—1B of FIG. 1A.
Figure 1C:
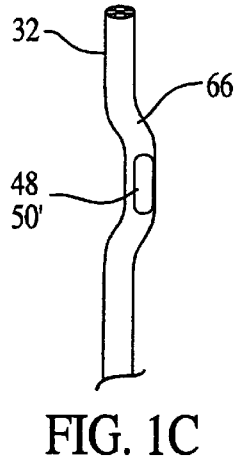
FIG. 1C is a detailed view of a portion of the catheter that includes an EMG electrode.

FIGS. 1A–1C illustrate a first embodiment of a monitoring catheter 30 according to the principles of the present invention. Monitoring catheter 30 inserts into the patient's esophagus and includes a body member 32 having a plurality of lumens 34 defined therein. Body member 32 is made from a biocompatible material suitable for use within the human body, such as a medical grade PVC with 35% Barium sulfate and having a durometer measurement of 90 Shore A. Other suitable materials for body member 30 include a medical grade polyurethane.

The entire length of the body member (or portions thereof) can be made from a radiopaque material to facilitate positioning the catheter in the patient. For example, a radiopaque strip can be provided down the length of the catheter. Alternatively, the radiopaque material can be provided at only the distal end portion of the body member because it is this portion of the catheter that is of primary interest while introducing the catheter into patient. The present invention also contemplates that no portion of the body member be made from a radiopaque material. Body member 32 is sized so as to be easily inserted into the patient's esophagus through the mouth or nose. Suitable exemplary sizes for body member 32 are 7 or 8 French (an outside diameter in a range of 2.3–2.7 mm) and a length of approximately 120 cm.

Catheter 30 includes a first pressure port 36 located at a distal end portion thereof and a second pressure port 38 spaced apart from first pressure port 36 along the length of body member 32 in a direction toward the proximal end. In the illustrated embodiment, pressure ports 36 and 38 are oval shaped. However, other configurations for the ports are contemplated by this invention. Each pressure port communicates with a separate lumen in body member 32 so that internal pressures at separate locations within the patient can be measured simultaneously. For example, the present invention contemplates that when catheter 30 is properly positioned within the patient, pressure port 36 measures gastric pressure and pressure port 38 measures esophageal pressure, simultaneously. In an exemplary embodiment of the present invention, lumen 40 communicates with first pressure port 36 and lumen 42 communicates with second pressure port 38. Although lumens 40 and 42 are illustrated in FIG. 1B as being generally circular in cross-section, it is to be understood that other shapes and locations for the lumens within the body member are possible.

In a preferred embodiment of the present invention, pressure sensing is accomplished using a liquid based pressure monitoring system. As such, lumens 40 and 42 are filled with a liquid, such as saline or water, and are coupled to pressure transducers (not shown) via pressure monitoring connectors 44 and 46, respectively, which are provided at the proximal end of catheter 30. An example of a suitable liquid based pressure transducer is the Cobe CDXpress 3 cc pressure transducer available from Cobe Laboratories Inc. of Lakewood, Colo. In this embodiment, a constant flow of liquid is provided to lumens 40 and 42 via connectors 44 and 46. Because pressure ports 36 and 38 are not sealed, the liquid drains from lumens 40 and 42, thereby keeping lumens 36 and 38 filled with liquid and preventing contaminants from entering the open lumens. The flow rate of liquid from lumens 40 and 42 is approximately 3 ml/hour under the control of a flow control device (not shown) that is also coupled to lumens 40 and 42 via connectors 44 and 46. An example of a suitable flow control device is the STERI-FLO™ Flush Device, which is incorporated into the Cobe CDXpress 3 cc pressure transducer.

It is to be understood, however, that the invention is not intended to be limited to the above described pressure sensing system. Other methods for sensing pressure, such as a balloon (gas or liquid filled) or an electronic pressure sensor, can be provided in place of one or both pressure ports. In short, this embodiment of the present invention contemplates providing at least two pressure detecting mechanisms on the body member of the monitoring catheter to measure the pressure within the patient at multiple locations.

Catheter 30 also includes a first electrode 48 and a second electrode 50 disposed on the exposed exterior surface of body member 32, preferably between pressure ports 36 and 38. Electrodes 48 and 50 are EMG electrodes that measure the activity of the patient's diaphragm when catheter 30 is properly positioned within the patient. In an exemplary embodiment of the present invention, electrodes 48 and 50 are each approximately 2 cm long and are disposed on body member 32 such that they extend along the longitudinal axis thereof. First and second electrodes 48 and 50 are sized and spaced apart so as to maximize the detection of diaphragm EMG signals while minimizing noise from other sources, such as cardiac activity, when the catheter is properly positioned within the patient. Electrodes 48 and 50 are made from a biocompatiable conducting material, such as silver filed vinyl and are coupled to an external EMG device (not shown) via leads 52 in lumen 54. More specifically, an EMG connector 56 at the proximal end of catheter 30 couples leads 52 to the EMG device.

Catheter 30 also includes a lumen 56 that extends the length thereof. Lumen 56 is sized and configured to receive a stylet 58 via a connector member 60 located at the proximal end of the catheter. Stylet 58 is a relatively rigid wire that, once inserted into the catheter via connector 60, is typically used by the physician to assist in introducing and guiding the catheter within the patient. One embodiment of the present invention contemplates providing stylet with a rounded distal tip 59 (see FIG. 1D) and/or reinforcing the distal end of lumen 56 so that stylet 58 does not punch through body member 32.

As noted above, electrodes 48 and 50 are EMG electrodes that measure the muscle activity of the patient's diaphragm. To maximize the operability of electrodes 48 and 50, it is important to ensure that the electrodes contact the patient's tissues, preferably as close to the diaphragm as possible. To accomplish this function, the present invention contemplates displacing first and/or second electrodes 48 and 50 from the longitudinal axis of body member 32 such that the first and/or second electrodes are farther from the longitudinal axis of the catheter than a majority of a remaining surface of the body member, thereby ensuring that first and/or second electrode 48 and 50 contact the patient's esophageal wall. There are a variety of techniques this electrode displacing function is accomplished by the present invention.

In one embodiment of the present invention, body member 32 includes a protrusion 62 located thereon, with electrode 48 and/or 50 disposed on the apex of the protrusion. See FIGS. 1A and 1B. It should be understood that electrode 48 and/or 50 can be provided at locations other than and/or in addition to the apex of the protrusion to ensure contact of the electrode with the patient. This embodiment contemplates that body member 32 and/or protrusion be structured so as to support protrusion 62 and the electrode to maintain the electrode against the esophageal wall while being large enough to cause the electrode to engage the esophageal wall. For example, one embodiment of the present invention contemplates that protrusion 62 is a partially inflated balloon that is collapsible enough to enable the protrusion to be inserted into the patient, yet inflated to an extent sufficient to engage the electrode with the esophageal wall once in the patient.

In another embodiment, body member 32 is provided with a "C" or "S" bend, with the electrode located at the outer convex portion of the bend to optimize positioning of the electrode to make contact with the patient. See FIG. 1C. The present invention further contemplates that a relatively straight stylet can be inserted into the catheter with the "C" or "S" bend. The flexible body member deforms to match the shape of the stylet, thereby straightening the catheter and making is easier to insert into the patient. Once inserted, the stylet is removed from the catheter so that the body member returns to its original shape, with a "C" or "S" bend therein. This embodiment contemplates that body member 32 is of sufficient elasticity and/or stiffness to support or maintain the electrode against the esophageal wall and that the bend is large enough to cause the electrode to engage the esophageal wall.

Figures 1D, 1E:
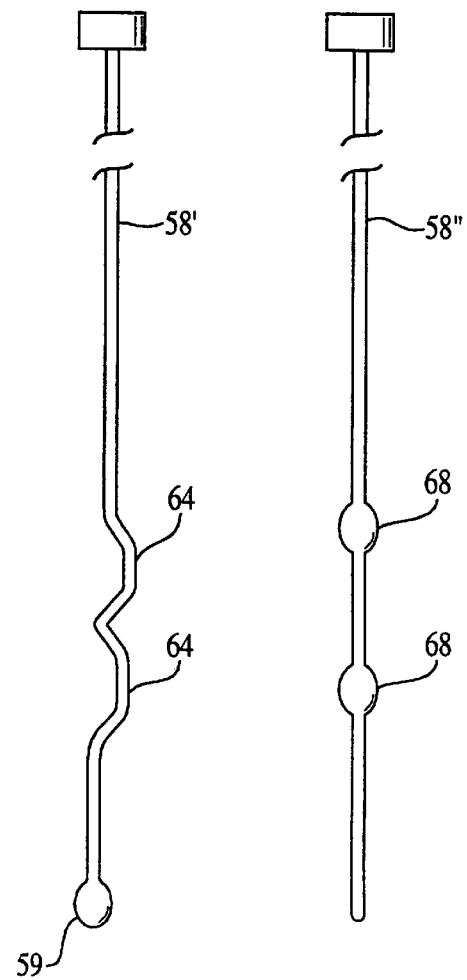
FIGS. 1D and 1E illustrate stylets for use with the monitoring catheter.

In another embodiment of the present invention, engaging EMG electrodes 48 and 50 with the esophageal wall is accomplished using the stylet, so that there is no need to increase the effective diameter of the undeflected catheter with a protrusion and/or provide bends on the catheter. In this embodiment, body member 32 is made from a relatively flexible material so that body member 32 conforms, i.e., deflects, to match the shape of the stylet. For example, providing a stylet 58' with the shape shown in FIG. 1D and inserting stylet 58' into lumen 56, causes body member 32 to assume the general shape of the stylet, as shown in FIG. 1C. More specifically, stylet 58' is provided with a "C" curve 64 at a location on the stylet that underlies each electrode once the stylet is properly inserted into the body member. The "C" curve in the stylet causes a portion 66 of body member 32 to assume the "C" curve shape of the stylet so that electrodes 48 and 50 securely engage the patient's esophageal wall. Other shapes for the stylet that cause the portion of the body member on which an electrode is mounted to deflect toward the esophageal wall are also contemplated by the present invention. For example, FIG. 1E illustrates a stylet 58" having bulbous portions 68 that distend the body member, including the electrodes located on the external surface thereof underlying the bulbous portion, to engage the electrodes with the esophageal wall.

It is to be understood that other techniques for ensuring that the EMG electrodes provided on the exposed surface of body member 32 engage the patient's esophageal wall are contemplated by the present invention. For example, a mechanism, such as a balloon, for distending the portion of the body member underlying the electrode can be provided in the catheter so that, once inflated, the balloon causes an electrode on the catheter to engage the esophageal wall. It is also possible to provide a balloon on a surface of the catheter so that inflating the balloon moves the portion of the body member having the electrode disposed thereon into contact with the patient's esophageal wall. Preferably, such a balloon is providing on a side of the body member opposite the electrode so that inflating the balloon shifts the entire portion of the body member, and, in particular, the electrode into contact with the patient.

In the above described embodiments of the present invention, proper contact between the electrodes and the esophageal wall is provided based on the shape of body member 32, e.g., shaping the body member or a stylet inserted therein to achieve this esophageal wall contact. It is to be understood, however, that the present invention also contemplates providing proper contact between the electrodes and the esophageal wall based on the shape of the electrodes themselves. For example, a further embodiment of the present invention contemplates making the electrodes sufficiently large to ensure that a proper contact is made with the esophageal wall. Along these lines, one embodiment of the present invention contemplates providing a stainless steel structure, such as a ball, in place of the strip electrode illustrated in FIGS. 1A and 1C. If the stainless steel structure is a ball, it can be slipped over the catheter and fixed in place at the same location as electrodes 48 and 50 in FIG. 1A. Such a structure, maximizes the electrical surface area that can contact the patient's esophageal wall. Of course, whatever the structure used for the electrodes, it is preferable that the structure not impair the normally biological function of the esophagus.

Monitoring catheter 30 can be inserted by itself into the patient's esophagus to monitor the physiological characteristics of the patient, such as the esophageal pressure, gastric pressure and/or diaphragm EMG. However, in many instances it is useful to use a catheter that is already in place in the patient's esophagus as a tracking guide for introducing monitoring catheter 30 in the patient. For example, patients in an ICU typically have a naso-gastric or oro-gastric feeding tube or suction tube located in their esophagus. The present invention contemplates using this previously positioned catheter, which is already introduced into the patient's esophagus, as a guide to place the monitoring catheter in the patient. In order to use the previously inserted catheter as a guide, the present invention contemplates providing catheter 30 with an attaching mechanism 70 that releaseably secures body member 32 to the previously inserted catheter without the need to disconnect or otherwise remove the existing catheter in the patient.

In the embodiment illustrated in FIG. 1A and in FIGS. 2A–2D, which are detailed perspective views of the distal end portion of catheter 30, attaching mechanism 70 includes a flexible guide line 72 having one end 74 fixed to the distal end portion of body member 32 and another end 76 that is selectively attachable to the distal end of body member 32 via a securing member. Guide line 72 and the securing member are made from any suitable biologically compatible material having sufficient strength and flexibility to function as described below.

Figure 2A:
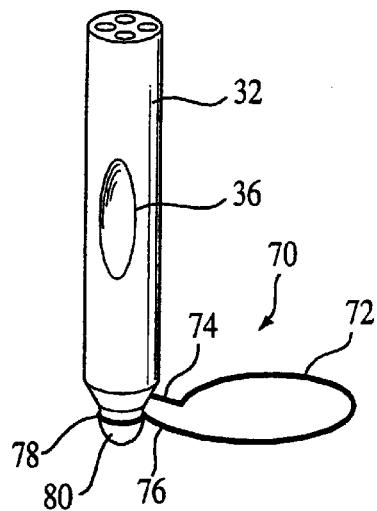
FIGS. 2A–2D are perspective views showing the operation of the monitoring catheter illustrated in FIGS. 1A–1C.

In the illustrated embodiment, the securing member is a locking loop 78 provided at end 76 of guide line 72. Also, the distal end of body member 32 in this embodiment has a pear-shaped tip 80. Pear-shaped tip 80 and locking loop 72 are sized and configured such that locking loop 72 attaches to tip 80 by slipping loop 72 over the wide portion of pear-shaped tip 80 and rests around neck 82. Once attached, as shown in FIG. 2A, for example, the guide line forms a guide loop that captures and secures the monitoring catheter to the second catheter.

It is to be understood, however, that the securing member, and, in particular, locking loop 78 can have a variety of configurations and can be made from a variety of materials. For example, loop 82 can be an elastic sleeve that slips over the distal tip of the catheter. Also, a variety of configurations are contemplated for the distal tip of the body member.

Figure 2B:
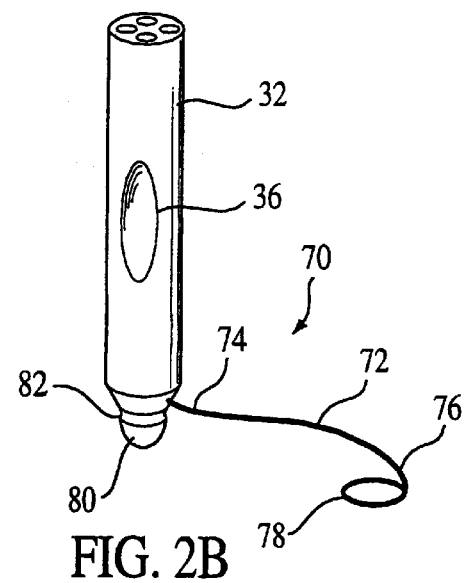
Figure 2C:
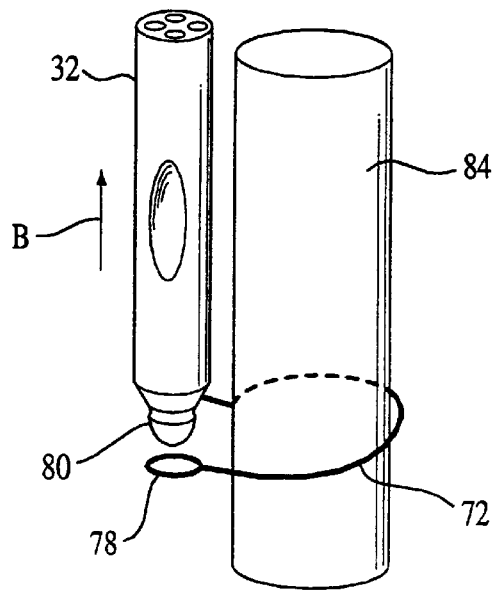
Figure 2D:
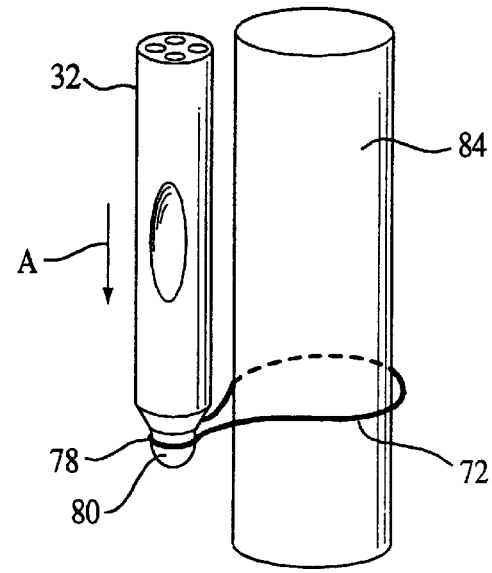

Inserting monitoring catheter 30 into a patient using a previously inserted catheter as a tracking guide involves first attaching the monitoring catheter to the existing catheter. Body member 32 attaches at its distal end to a second catheter 84, which, as noted above, is preferably already inserted into the patient, by first disengaging locking loop 78 from the tip of body member 32, as shown in FIG. 2B. In the illustrated embodiment, guide line 72 is wrapped around second catheter 84 and attaches to pear-shaped tip 80 by slipping locking loop 78 over tip 80, thereby capturing second catheter 84 via guide line 72, as shown in FIG. 2D. The length of guide line 72 and, hence, the diameter of the guide loop, determines the ease at which the monitoring catheter tracks or slides along the second catheter. For conventional feeding tubes, guide line 72 is typically between 10 mm–15 mm. Catheter 30, once attached to the previously inserted catheter, is inserted into the patient's esophagus by moving body member 32 in the direction indicated by arrow A in FIG. 2D. The stylet can be used to move catheter 30 along the previously placed catheter.

Guide line 72 remains closed around the second catheter as the catheter is inserted into the patient, i.e., moves in the direction of arrow A. However, it is also beneficial for monitoring catheter 30 to disengage from the previously placed catheter, when necessary, for example, when the monitoring catheter is to be removed from the patient leaving the previously inserted catheter in place. In the illustrated embodiment, this is accomplished by releasing locking loop 78 from the distal tip of catheter 30. Removing locking loop 78 from the tip of the catheter is accomplished by applying a pulling force on loop 78 also in the direction of arrow A. Such a pulling force occurs when the catheter begins to be removed from the patient, as indicated by arrow B in FIG. 2C. The tendency of the guide line to remain in place on the previously placed catheter, i.e., resistance to pull-out, provides the force necessary to remove the locking loop from the distal tip of the catheter.

The amount of force necessary to remove the locking loop from the distal tip of the catheter can be controlled based on the size of locking loop 78, its elasticity, and/or the size and shape of the catheter tip, as well as the placement position of the locking loop on the tip. Preferably, the pulling force necessary to release the locking loop from tip 80 is small enough so that release occurs upon initiating withdrawal of the catheter from the patient but is large enough that release does not accidentally occur due to a slight pull on the catheter. Thus, catheter 30 releases from the previously placed catheter when catheter 30 starts to be pulled out of the patient with the previously inserted catheter remaining in place. See FIG. 2C. The monitoring catheter can also be removed along with the previously inserted catheter or left in place by itself upon removal of the previously placed catheter.

Figure 3A:
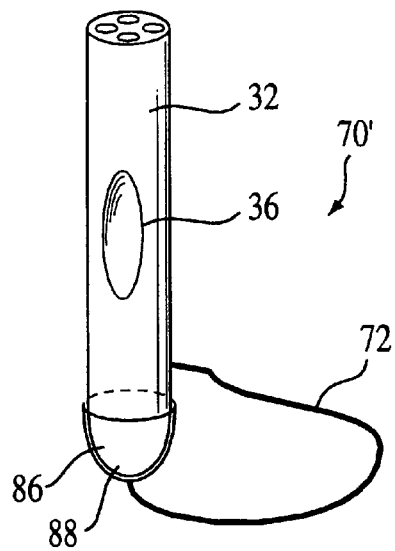
FIGS. 3A–3D are perspective views showing the operation of a second embodiment of a monitoring catheter according to the principles of the present invention.
Figure 3B:
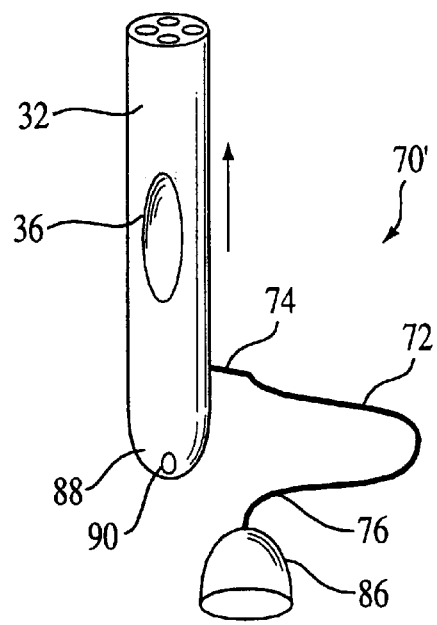
Figure 3C:
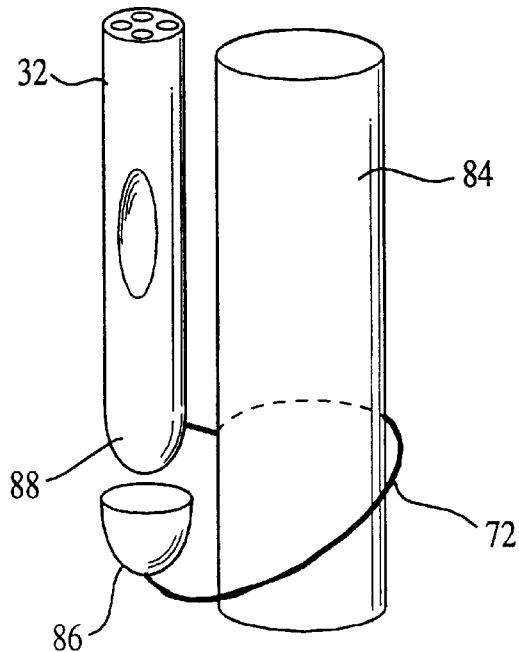
Figure 3D:
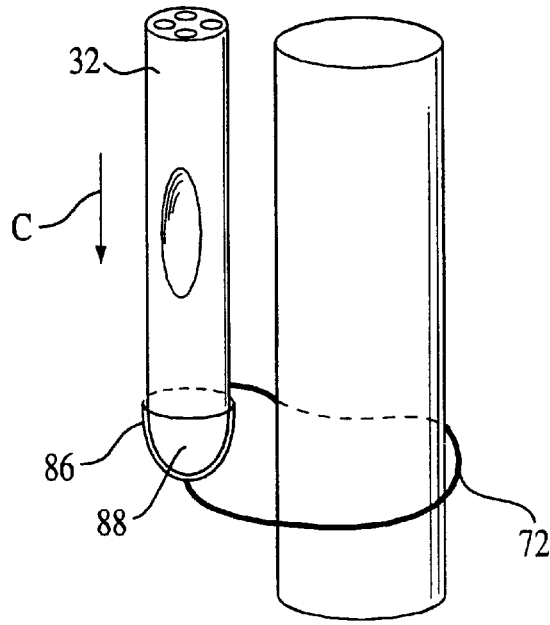

It is to be understood that other configurations for attaching mechanism 70 are contemplated by the present invention. An alternative embodiment of attaching mechanism 70' is illustrated in FIGS. 3A–3D. This embodiment of attaching mechanism 70' is similar to that illustrated in FIGS. 2A–2D except that instead of the securing member being a locking loop 78, the securing member is a cup 86 that is sized and configured to slip on, and remain on, distal tip 88 of body member 32 in the absence of a releasing force. As shown in FIGS. 3C and 3D, body member 32 attaches to second catheter 84, which is preferably already in place in the patient, by wrapping guide line 72 around the previously placed catheter and slipping cup 86 over tip 88 of body member 32. The assembly can then by tracked along second catheter 84 in the direction of arrow C to place the monitoring catheter at its proper location in the patient. As with the locking loop in the previous embodiment, cup 86 releases from distal tip 80 by applying a pulling force on body member 32. The friction of guide line 72 on the previously placed catheter tends to hold cup 86 in place during removal of the monitoring catheter (assuming the previously inserted catheter remains in place), thereby causing the cup to slip off distal tip 80 of body member 32. The amount of pulling force necessary to release cup 86 from tip 88 is determined by the size and shape of the cup and/or distal tip 80, the elasticity of cup 86, and/or the placement position of the cup on the catheter tip.

A further embodiment of the present invention contemplates providing the monitoring catheter with a selectively actuateable mechanism to assist in disengaging cup 86 from body member 32. One example of such a disengaging mechanism is to extend a lumen, such as stylet lumen 56 or a separate dedicated lumen, to distal tip 80 of the monitoring catheter. A port 90, which is defined in tip 80 at a location underlying cup 86 when the cup is positioned on the distal tip, communicates with the lumen. The lumen carries a liquid, such as water or saline, that is injected therein at the proximal end of the catheter. The lumen carries the liquid from the proximal end to port 90. Because cup 86 covers port 90 when mounted on tip 80, the liquid being forced from port 90 ejects cup 86 from the tip of the catheter. Furthermore, the cup-like shape of the securing member maximizes the inside surface area against which the liquid is dispensed, thereby making it easier for the cup to be dislodged. In an exemplary embodiment of the present invention, port 90 is coupled to the same lumen that accommodates the stylet. With the stylet removed, a syringe is used to inject approximately 3 ccs of water or saline into the lumen, thereby disengaging cup 86 from the catheter.

Attaching mechanisms 70 and 70' are two exemplary techniques for attaching the monitoring catheter to a previously placed catheter. It is to be understood, however, that other attaching techniques are contemplated by the present invention. For example, rather than provide a cup at the end of guide line 72 as in the embodiment illustrated in FIGS. 3A–3D, a plug can be used. The plug, like the cup, attaches to guide line 72, but, unlike the cup, inserts into a slot, groove or other receiving structure in the distal end of body member 32. The plug and the structure in body member 32 receiving the plug can have a variety of configurations so long as they function to selectively attach the guide line to the monitoring catheter so that the monitoring catheter can be selectively attached to a previously placed catheter, thereby using the previously placed catheter as a tracking guide. Also, the disengaging mechanism discussed above with respect to cup 86, i.e., the use of a liquid injected into a lumen to force the cup off the catheter, can be used with the plug.

Further embodiments of the present invention contemplate other techniques for disengaging the monitoring catheter from the previously placed catheter. For example, any portion of the attaching mechanism can be made from a biologically compatible material that dissolves after being in the body a certain amount of time. Once the material dissolves, the monitoring catheter is free of the previously placed catheter.

Another embodiment of the present invention contemplates that the structures of the attaching mechanism can be made to break apart from one another to free the monitoring catheter from the previously placed catheter. For example, locking loop 78 or cup 86 can be attached to guide line 72 such that guide line 72 detaches from locking loop 78 or cup 86 when the catheter starts to be removed from the patient. In which case, the locking loop or cup need not be selectively attachable to the catheter. Instead, once attached, the locking loop or cup can remain fixed to the catheter with some other portion of the attaching mechanism releasing, disengaging or dissolving to detach the monitoring catheter from the previously placed catheter.

Yet other embodiments of the present invention contemplate providing other mechanisms that cause the various components of the attaching mechanism to detach from one another or break apart, thereby freeing the monitoring catheter from the previously placed catheter. For example, the distal end of body member 32 to which the locking loop, cup or other structure is attached can be expanded by a balloon, for example, to cause the locking loop, cup or other structure to break apart. Similarly, the monitoring catheter can be moved from the previously placed catheter, using a balloon, for example, thereby causing a portion of the attaching mechanism, such as the guide line, to break or disengage. It should be understood that each of the techniques discussed above can be used alone or in combination with other techniques to accomplish the function of disengaging the monitoring catheter from the previously placed catheter.

Figure 4A:
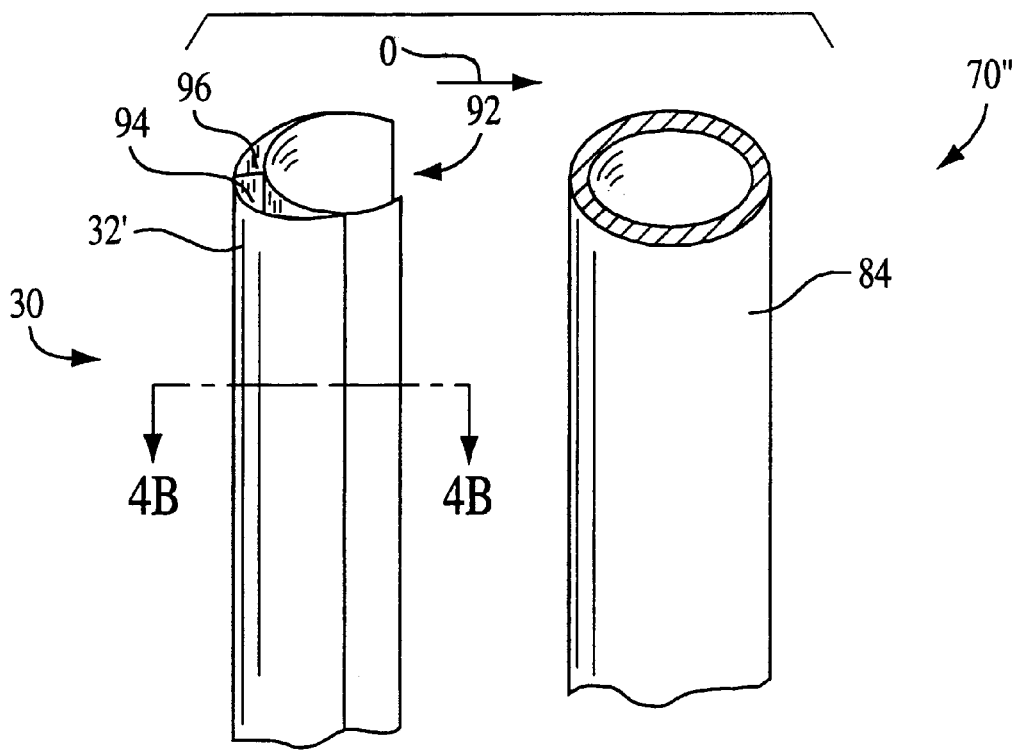
FIG. 4A is a perspective view of a third embodiment of a monitoring catheter according to the principles of the present invention.
Figure 4B:
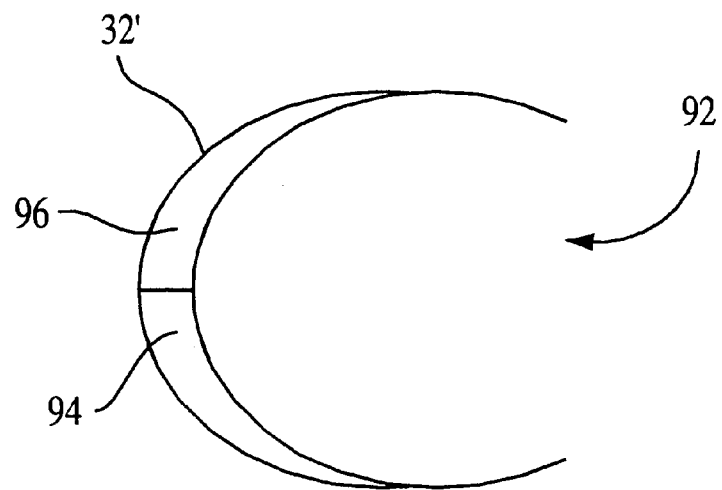
FIG. 4B is a cross-sectional view of the monitoring catheter taken along line 4B—4B of FIG. 4A.

Yet another embodiment of an attaching mechanism 70" is illustrated in FIGS. 4A–4B. In this embodiment, body member 32' has a cavity 92 defined therein. Cavity 92 is sized so as to receive previously placed catheter 84 therein. In essence, the monitoring catheter, or a portion thereof, snaps onto the previously placed catheter, thereby enabling the monitoring catheter to track along the previously placed catheter during insertion. As shown in FIGS. 4A and 4B, body member 32' includes two lumens 94 and 96. It is to be understood, however, that additional lumens, as well as the features of the previous embodiments discussed above, can be incorporated into the embodiment illustrated in FIGS. 4A–4B. For example, a stylet can be used to distend the wall of body member 32' to cause the electrodes (not shown) to engage the patient's esophageal wall.

Figure 5:
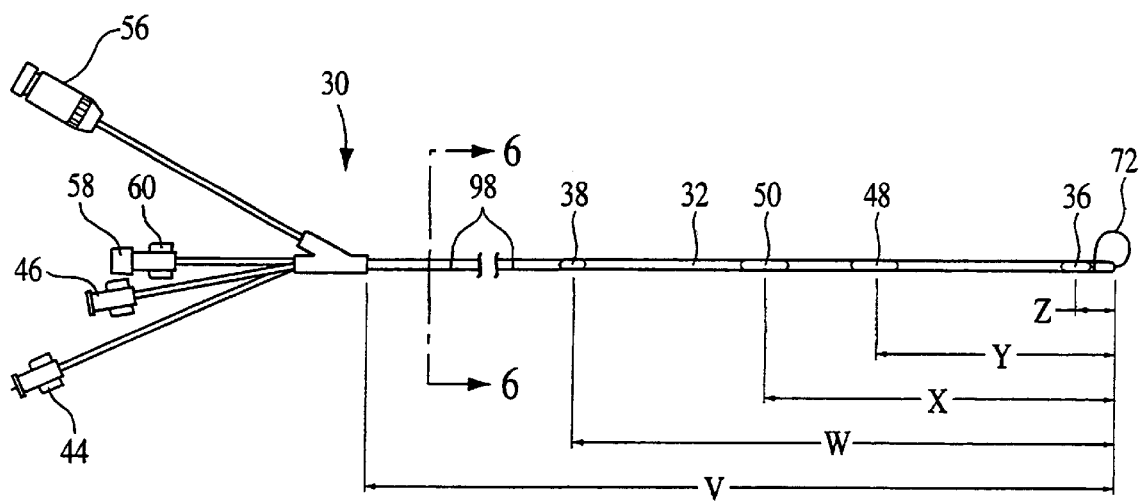
FIG. 5 is a side view of a first embodiment of a monitoring catheter showing the relative distances of the various components of the catheter from the distal tip.
Figure 6:
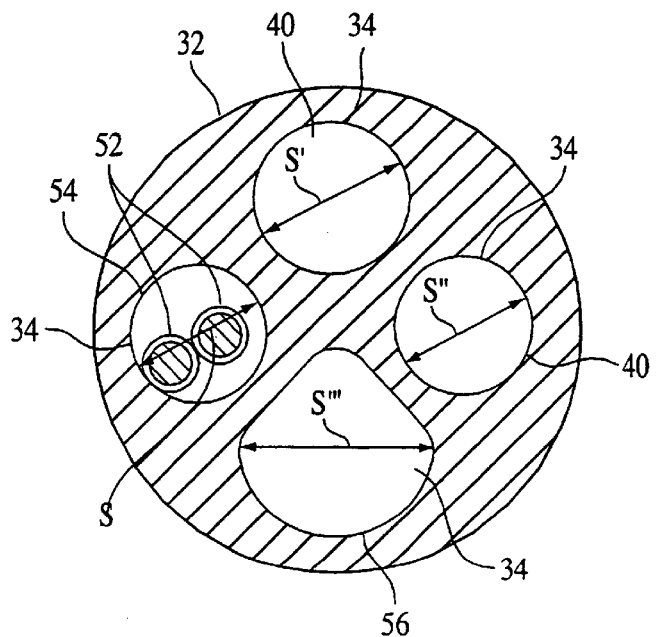
FIG. 6 is a cross sectional view of the monitoring catheter similar taken along line 6—6 of FIG. 5, showing the relative dimensions of the lumens and the catheter according to one embodiment of the present invention.

FIGS. 5 and 6 illustrate monitoring catheter 30 according to a presently preferred embodiment. These figures provide an example of the dimensions and/or typical distances between the various components of the monitoring catheter. Possible dimensions of the distances designated by V, W, X, Y and Z in FIG. 5 may be the following: V=120.0 cm; W=23.0 cm; X=15.0 cm; Y=10.0 cm; and Z=1.5 cm. Possible dimensions of S, S', S", and S'" of lumen 34 of FIG. 6 may be 0.030", 0.035", 0.030" and 0.045", respectively. However, the present invention is not intended to be limited to the dimensions and/or distances illustrated in FIGS. 5 and 6.

As shown in FIG. 5, properly positioning monitoring catheter 30 in the patient is assisted by providing depth markings 98 on the external surface of body member 32. The physician uses these marking to gauge the distance the catheter has been inserted. Furthermore, by providing a pair of pressure monitoring ports 36 and 38 spaced apart from one another along the length of body member 32, the physician inserting the monitoring catheter is able to discern how far the catheter has been inserted into the patient based on the output from the pressure sensors coupled to these ports. If both pressure sensors are outputting substantially the same pressure waveform, this indicates that both pressure ports are, for example, located in the esophagus and measuring esophageal pressure. If, however, the waveforms are not the same, and, more specifically, opposite, this indicates that one pressure port is measuring gastric pressure and the other is measuring esophageal pressure, because these pressure are typically inversely related. Thus, the outputs from the monitoring catheter itself assist the physician in properly placing the catheter in the patient. As noted above, the present invention also contemplates providing a radiopaque material along the length or at selected locations on the monitoring catheter, such as the distal tip, to assist the caregiver in positioning the catheter in the patient.

Alternative configurations of the present invention include providing only one EMG electrode on the monitoring catheter, with the other electrode being disposed outside the patient or on a separate structure within the patient. A suitable separate structure for providing the other EMG electrode in the patient could include another monitoring catheter of similar design and/or configuration to that disclosed above according to the present invention. The present invention also contemplates providing additional pressure ports and lumens in the monitoring catheter, or any other type of pressure sensing system, for measuring the patient's internal pressures additional locations. Furthermore, the present invention contemplates providing other sensors on or in conjunction with the monitoring catheter. Examples of other sensors suitable for use with the monitoring catheters discussed above include: a temperature sensor, a PH electrode, a microphone, an echocardiogram and/or ultrasound transducer, $PO_2$ electrodes for gastric tonometry, $PCO_2$ and EKG electrodes. In addition, the present invention contemplates providing active electrodes on the monitoring catheter, such as a defibrillator device and pacing (cardiac and/or diaphragm) electrodes, instead of or in addition to the above mentioned passive monitoring devices. The signal detected by the monitoring catheter of the present invention can be used for a variety of purposes. For example, the diaphragm EMG signal can be used to control a ventilator. In addition, airway resistance and lung compliance can also be measured. The information gathered using the monitoring catheter of the present invention can also be used for exercise testing and sleep studies of the patient.

FIGS. 1A–1E illustrate various configurations for the catheter, electrodes, and/or stylet that are used to ensure good contact between the electrodes and the patient's tissues, which is important in obtaining a raw EMG signal with a minimal amount of noise. In addition to these techniques, or in the alternative, the present invention also contemplates locating the electrodes on the catheter and providing a circuit to which the electrodes are connected that maximizes the quality of the raw EMG signal. Details of this electrode placement and several exemplary circuit configurations are discussed below with reference to FIGS. 7–10.

Figure 7:
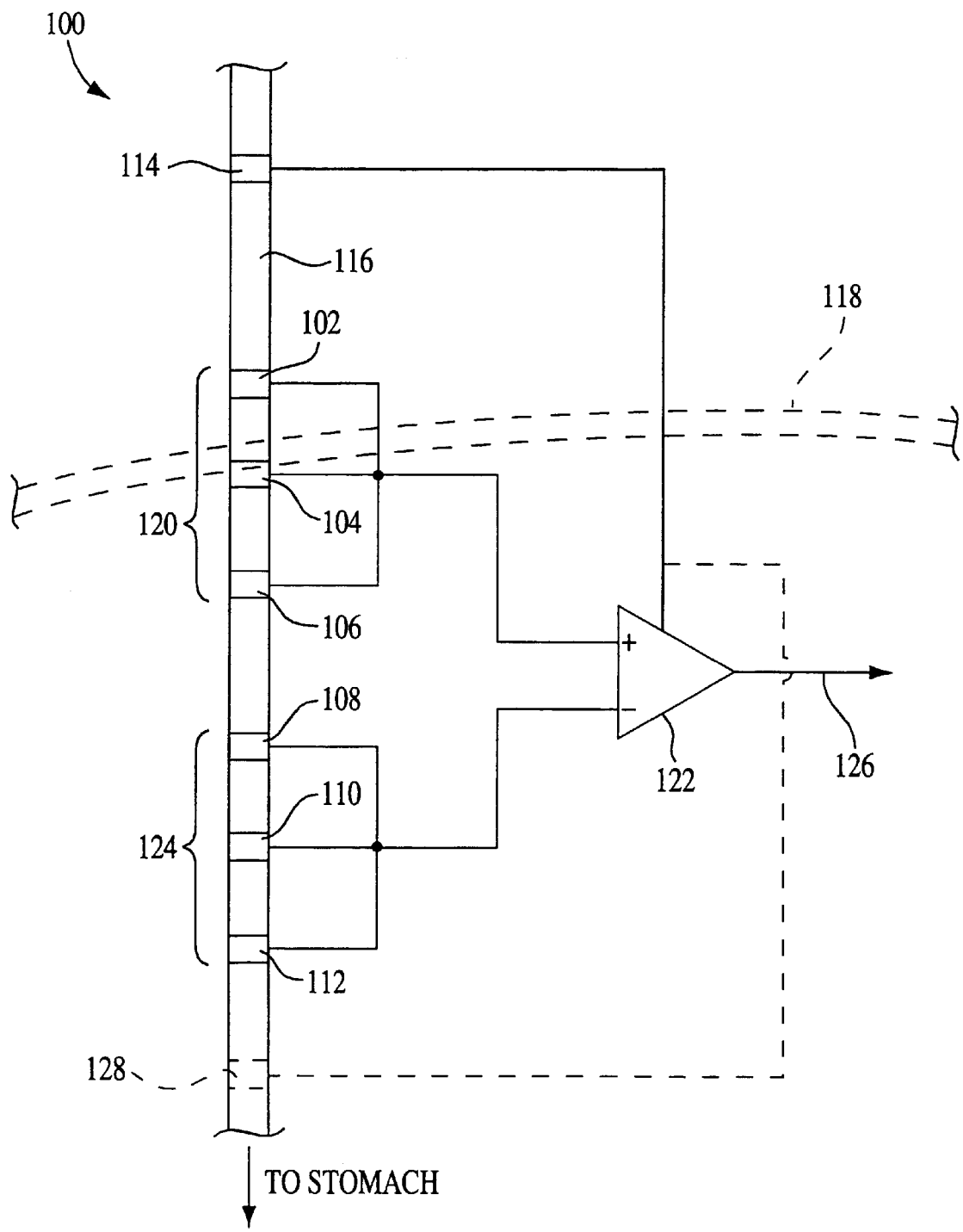
FIG. 7 is a schematic diagram of a monitoring catheter including a first configuration for circuitry associated with the electrodes on the catheter.

FIG. 7 illustrates a monitoring catheter 100 according to the principles of the present invention in which a plurality of electrodes 102–114 are disposed on a body member 116 of the catheter. In this embodiment, electrodes 102–114 are ring electrodes, where each ring is approximately 4 mm in height and spaced approximately 12 mm apart. Each ring is preferably made from platinum or medical grade stainless steel. FIG. 7 schematically shows the patient's diaphragm 118 to show how the electrodes are positioned on the catheter to ensure that at least one of the electrodes is proximate the diaphragm when the catheter is properly inserted in the patient's esophagus.

In the embodiment illustrated in FIG. 7, a first group of electrodes 120 are electrically coupled to one another effectively forming a long electrode that provides one input to a differential amplifier 122. In this embodiment, electrodes 120 function as sensing electrodes in that they are located proximate to diaphragm 118 to detect the diaphragm EMG signals. A second group of electrodes 124 are also electrically coupled to one another to provide a second input to differential amplifier 122 to function as a reference electrode. Preferably, electrodes 124 are located far enough away from diaphragm when the catheter is properly inserted in the patient so that little or no diaphragm EMG signals are picked up by electrodes 124, thereby maximizing the diaphragm EMG signal included in a raw EMG signal 126 output from differential amplifier 122.

Monitoring catheter 100 also includes an isolated ground electrode 114 that is operatively coupled to differential amplifier 122. The present inventors discovered that such an isolated ground electrode at a uppermost location on body member 116 coupled to the differential amplifier functions as a guard electrode, much the same way a shield electrode functions on a coaxial cable, thereby improving the signal to noise ratio in raw EMG signal 126. The shielding function provided by electrode 114 is enhanced by providing an optional second isolated ground electrode 128 at a lower most location on body member 116.

While FIG. 7 illustrates coupling three electrodes to define electrode groups 120 and 124, it is to be understood that more electrodes or less electrodes can be coupled to define each electrode group. Similarly, additional isolated ground electrodes can be provided proximate to electrodes 114 and 128. Furthermore, those skilled in the art would understand that the specific size, spacing and configurations for the electrodes can be varied to optimize the positioning of the electrodes within the patient.

Figure 8:
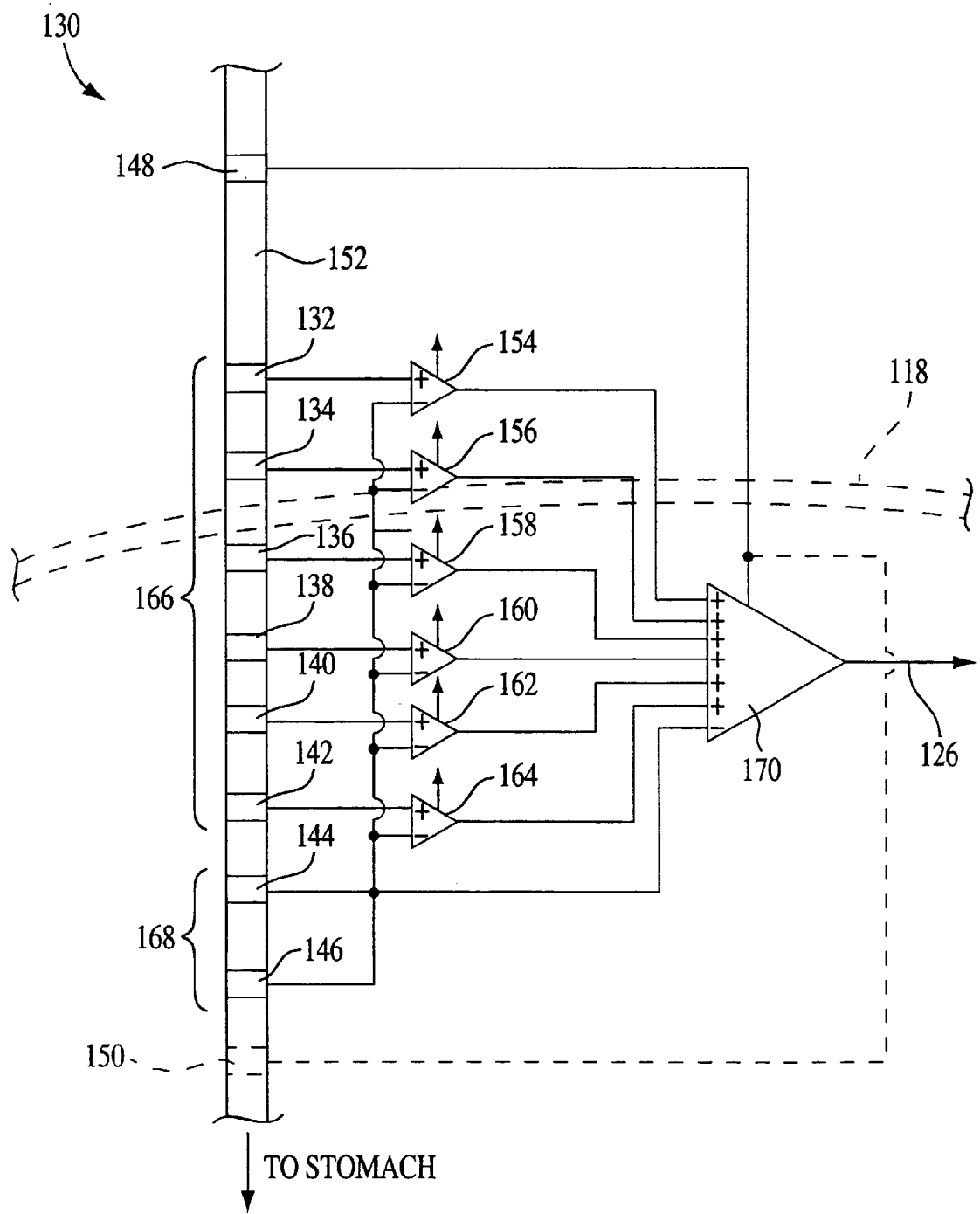
FIG. 8 is a schematic diagram of a monitoring catheter including a second configuration for circuitry associated with the electrodes on the catheter.

FIG. 8 illustrates another embodiment for a monitoring catheter 130 according to the principles of the present invention, in which a plurality of electrodes 132–150 are disposed on a body member 152 of the catheter. As in the previous embodiment, electrodes 132–150 are ring electrodes and are spaced apart from one another along a portion of the length of body member 152. In this embodiment, electrodes 132–142 in a first group of electrodes 166 function as sensing electrodes and are each connected to one input of an associated isolation amplifier 154–164. Electrodes 144 and 146 in a second group of electrodes 168 are electrically coupled to one another and serve as the reference electrode for each isolation amplifier 154–164. The output of each isolation amplifier is provided to a summing amplifier 170. In addition, the reference electrode 168 is also provided as an input to summing amplifier 170, which outputs raw EMG signal 126. The configuration illustrated in FIG. 8 is advantageous in that each sensing electrode in group 166 is acted upon individually to maintain the integrity of each signal from each electrode, rather than connecting a plurality of electrodes as in FIG. 7.

As with the embodiment illustrated in FIG. 7, monitoring catheter 130 of FIG. 8 includes an isolated ground electrode 148 as the outermost electrode in the series of electrodes provided on body member 152. In addition, the present invention contemplates providing a second isolated ground electrode 150 at the other end of the series of electrodes also at an outermost position. One, or preferably both isolated ground electrodes 148 and 150 are operatively coupled to isolation amplifiers 154–164 and to summing amplifier 170 as is known in the art to function as shield electrodes, thereby minimizing the noise present in raw EMG signal 126.

Figure 9:
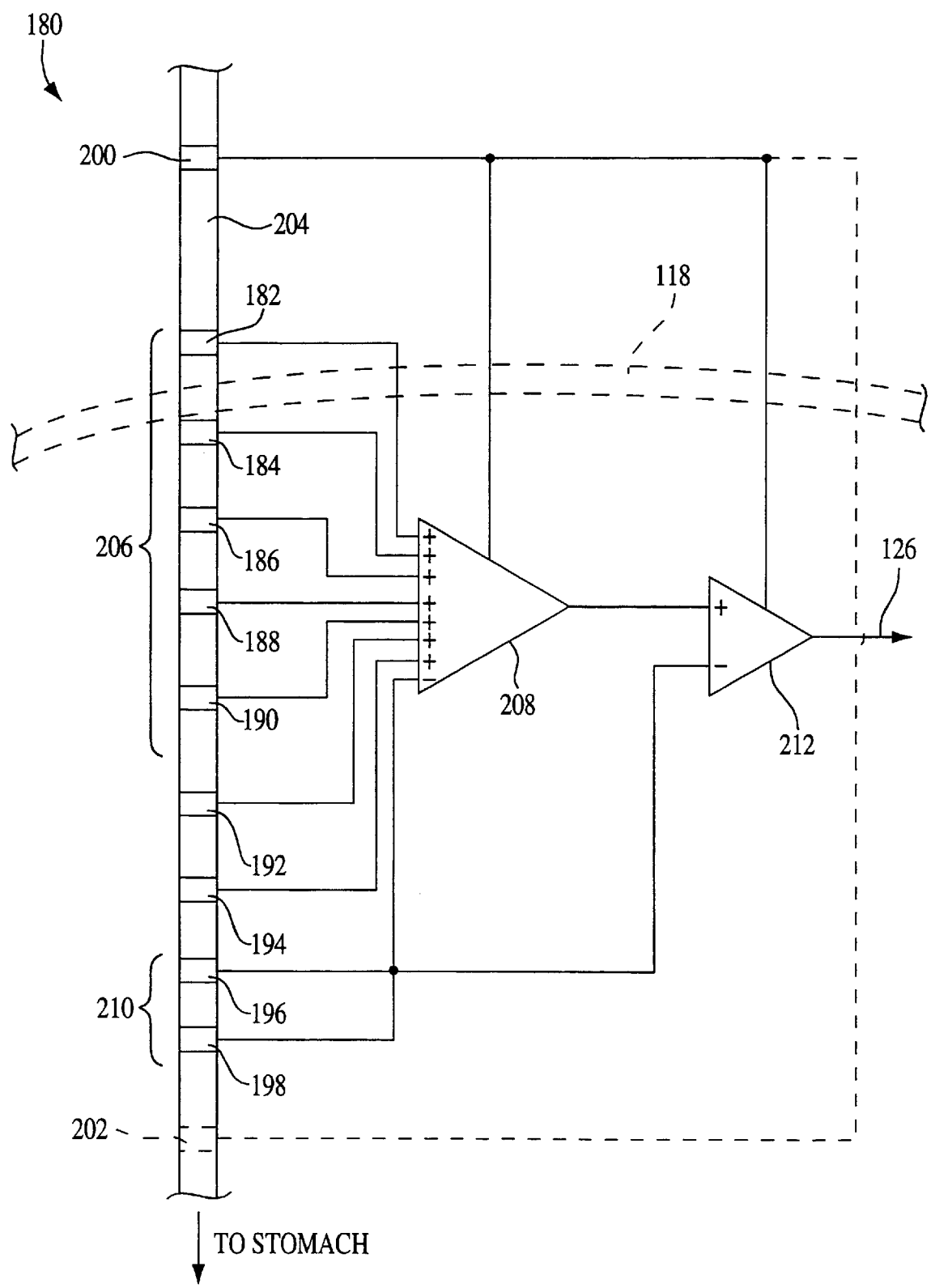
FIG. 9 is a schematic diagram of a monitoring catheter including a third configuration for circuitry associated with the electrodes on the catheter.

FIG. 9 illustrates yet another embodiment for a monitoring catheter 180 according to the principles of the present invention, in which a plurality of electrodes 182–202 are disposed on a body member 204 of the catheter. As in the embodiment shown in FIGS. 7 and 8, electrodes 182–202 are ring electrodes and are spaced apart from one another along a portion of the length of body member 204. In this embodiment, electrodes 182–194 in a first group of electrodes 206 function as sensing electrodes and are connected to a summing amplifier 208. Electrodes 144 and 146 in a second group of electrodes 210 are electrically coupled to one another and serve as the reference electrode for summing amplifier 208. The output of the summing amplifier is provided to a differential amplifier 212. In addition, the reference electrode 210 is also provided as an input to differential amplifier 170, which outputs raw EMG signal 126.

As with the embodiments illustrated in FIGS. 7 and 8, monitoring catheter 180 of FIG. 9 includes an isolated ground electrode 200 as the outermost electrode in the series of electrodes provided on body member 204. In addition, the present invention contemplates providing a second isolated ground electrode 202 at the other end of the series of electrodes also at an outermost position. One, or preferably both isolated ground electrodes 200 and 202 are operatively coupled to summing amplifier 208 and to differential amplifier 212 as is known in the art to function as shield electrodes, thereby minimizing the noise present in raw EMG signal 126.

Figure 10:
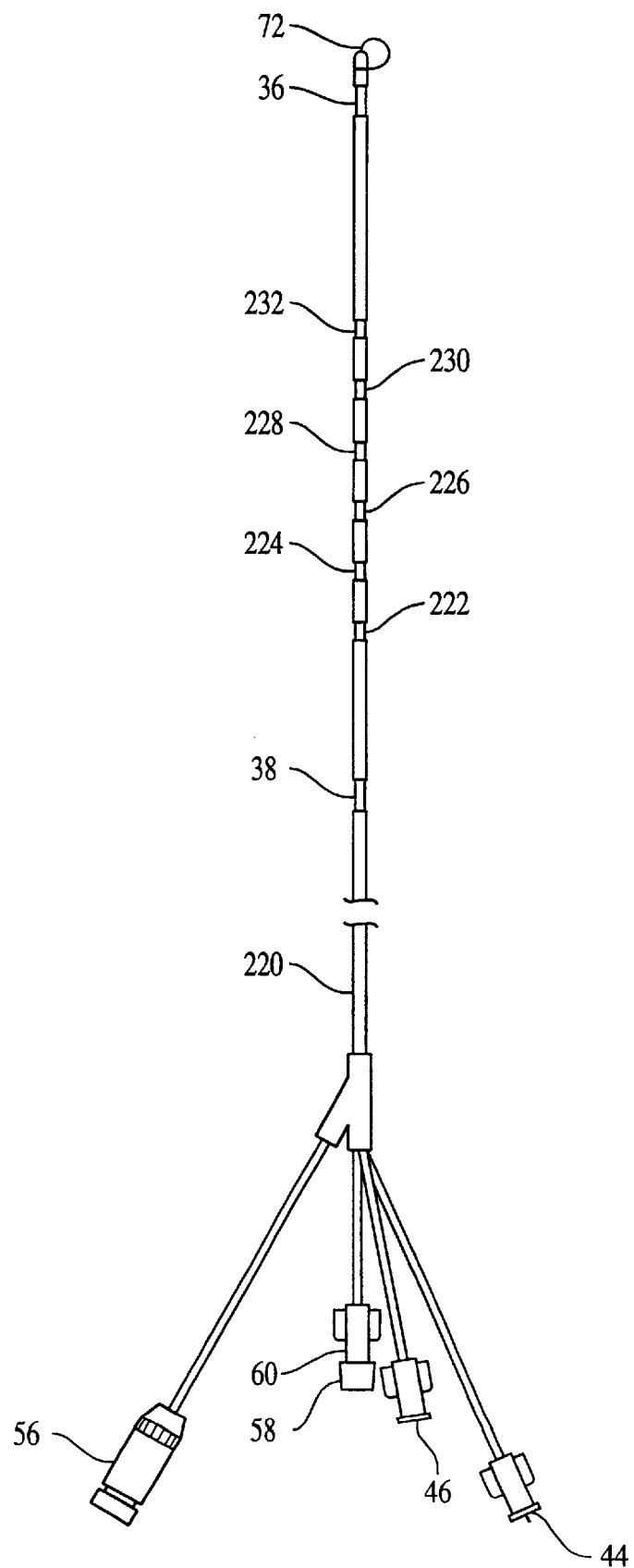
FIG. 10 is a side view of another embodiment of a monitoring catheter showing the relative distances of the various components of the catheter from the distal tip.

FIG. 10 illustrates a monitoring catheter 220 according to another embodiment of the present invention. Catheter 220 includes a plurality of electrodes 222–232 for connection to a circuit such as those circuits discussed above with respect to FIGS. 7–9. In addition, monitoring catheter 220 includes first and second pressure ports 36 and 38, pressure monitoring connectors 44 and 46, an EMG electrical connector 56, and a stylet 58 shown fully inserted into catheter 220 via a connector member 60. It can thus be appreciated that the monitoring catheter of the present invention provides in one device a plurality of sensing elements to provide a caregiver with valuable information helpful in properly treating and diagnosing the patient. Furthermore, the catheter can be used in conjunction with an existing catheter that has been previously inserted into the patient, such as a naso-gastric or oro-gastric catheter, thereby making it easier for the physician to place the monitoring catheter in the patient while minimizing the likelihood of an incorrect placement.

Although the invention has been described in detail for the purpose of illustration based on what is currently considered to be the most practical and preferred embodiments, it is to be understood that such detail is solely for that purpose and that the invention is not limited to the disclosed embodiments, but on the contrary, is intended to cover modifications and equivalent arrangements that are within the spirit and scope of the appended claims.

What is claimed is:

1. A monitoring catheter comprising:
   (a) a body member;
   (b) a first electrode disposed on a first portion of the body member, the first electrode having a first lead coupled thereto, the first lead extending from the first electrode to a proximal end of the body member;
   (c) a second electrode disposed on a second portion of the body member, the second electrode having a second lead coupled thereto, the second lead extending from the second electrode to the proximal end of the body member, the first electrode and the second electrode being sized, configured, and spaced from one another so as to maximize detection of diaphragm muscle activity while minimizing noise; and
   (d) an attaching mechanism that releaseably secures the body member to a second catheter, wherein the attaching mechanism includes:
      (1) a guide line having a first portion coupled to a portion of the body member, and
      (2) a securing member provided at a second portion of the guide line, the securing member and a distal end portion of the body member being configured such that the securing member selectively attaches to the distal end portion of the body member, thereby capturing a second catheter via a guide loop defined by the guide line, wherein the securing member is one of: (i) a locking loop provided at the second portion of the guide line, the locking loop being sized such that the locking loop selectively slips over a portion of the distal end portion of the body member, and (ii) a cup provided at the second portion of the guide line, the cup being sized and configured such that the cup selectively attaches to the distal end portion of the body member so as to capture a second catheter via the guide line.

2. A monitoring catheter comprising:
   (a) a body member;
   (b) a first electrode disposed on a first portion of the body member, the first electrode having a first lead coupled thereto, the first lead extending from the first electrode to a proximal end of the body member;
   (c) a second electrode disposed on a second portion of the body member, the second electrode having a second lead coupled thereto, the second lead extending from the second electrode to the proximal end of the body member, the first electrode and the second electrode being sized, configured, and spaced from one another so as to maximize detection of diaphragm muscle activity while minimizing noise; and
   (d) an attaching mechanism that releaseably secures the body member to a second catheter, wherein the attaching mechanism includes a cavity defined within the body member, the cavity being sized and structured such that the second catheter is adapted to be selectively secured within the cavity.

3. A monitoring catheter comprising:
   (a) a body member;
   (b) a first electrode disposed on a first portion of the body member, the first electrode having a first lead coupled thereto, the first lead extending from the first electrode to a proximal end of the body member;
   (c) a second electrode disposed on a second portion of the body member, the second electrode having a second lead coupled thereto, the second lead extending from the second electrode to the proximal end of the body member, the first electrode and the second electrode being sized, configured, and spaced from one another so as to maximize detection of diaphragm muscle activity while minimizing noise;
   (d) a third electrode disposed on a third portion of the body member, the third electrode having a third lead coupled thereto, the third lead extending from the third electrode to a proximal end of the body member; and
   (e) a differential amplifier having a first input, a second input, and a ground terminal, the first electrode being operatively connected to the first input via the first lead, the second electrode being operatively connected to the second input via the second lead, and the third electrode being operatively connected to the ground terminal via the third lead.

4. A monitoring catheter comprising:

(a) a body member;

(b) a first electrode disposed on a first portion of the body member, the first electrode having a first lead coupled thereto, the first lead extending from the first electrode to a proximal end of the body member, wherein the first electrode is defined by a plurality first electrode members disposed along a length of the body member, each first electrode member having a lead coupled thereto extending from the associated first electrode member to a proximal end of the body member;

(c) a second electrode disposed on a second portion of the body member, the second electrode having a second lead coupled thereto, the second lead extending from the second electrode to the proximal end of the body member, the first electrode and the second electrode being sized, configured, and spaced from one another so as to maximize detection of diaphragm muscle activity while minimizing noise;

(d) a third electrode disposed on a third portion of the body member, the third electrode having a third lead coupled thereto, the third lead extending from the third electrode to a proximal end of the body member;

(e) a plurality of isolation amplifiers each having a first input and a second input, a ground terminal, and an output, each first electrode member being operatively coupled to a first input of an associated isolation amplifier via the associated lead, the second electrode being operatively connected to the second input of each isolation amplifier via the second lead, and the third electrode being operatively connected to the ground terminal of each isolation amplifier via the third lead; and (f) a summing amplifier receiving as an input the output from each isolation amplifier and having another input operatively coupled to the second electrode via the second lead, the summing amplifier also having a ground terminal operatively coupled to the third electrode via the third lead.

5. A monitoring catheter comprising:

(a) a body member;

(b) a first electrode disposed on a first portion of the body member, the first electrode having a first lead coupled thereto, the first lead extending from the first electrode to a proximal end of the body member, wherein the first electrode is defined by a plurality first electrode members disposed along a length of the body member, each first electrode member having a lead coupled thereto extending from the associated first electrode member to a proximal end of the body member;

(c) a second electrode disposed on a second portion of the body member, the second electrode having a second lead coupled thereto, the second lead extending from the second electrode to the proximal end of the body member, the first electrode and the second electrode being sized, configured, and spaced from one another so as to maximize detection of diaphragm muscle activity while minimizing noise;

(d) a third electrode disposed on a third portion of the body member, the third electrode having a third lead coupled thereto, the third lead extending from the third electrode to a proximal end of the body member;

(e) a summing amplifier having inputs operatively coupled to each first electrode member via an associated lead and to the second electrode, the summing amplifier also having a ground terminal operatively coupled to the third electrode via the third lead and an output; and (f) a differential amplifier having a first input, a second input, and a ground terminal, the output of the summing amplifier being operatively connected to the first input, the second electrode being operatively connected to the second input via the second lead, and the third electrode being operatively connected to the ground terminal via the third lead.

6. A monitoring catheter comprising:

(a) a body member;

(b) a first pressure detecting mechanism disposed at a first portion of the body member;

(c) a second pressure detecting mechanism disposed at a second portion of the body member, the second pressure detecting mechanism being spaced apart from the first pressure detecting mechanism along a length of the body member; and (d) an attaching mechanism that releaseably secures the body member to a second catheter, wherein the attaching mechanism includes:

(1) a guide line having a first portion coupled to a portion of the body member, and (2) a securing member provided at a second portion of the guide line, the securing member and a distal end portion of the body member being configured such that the securing member selectively attaches to the distal end portion of the body member thereby capturing a second catheter via the guide line, wherein the securing member is one of (i) a locking loop provided at the second portion of the guide line, the locking loop being sized such that the locking loop selectively slips over a portion of the distal end portion of the body member and (ii) a cup provided at the second portion of the guide line, the cup being sized and configured such that the cup selectively attaches to the distal end portion of the body member so as to capture a second catheter via the guide line.

7. A monitoring catheter comprising:

(a) a body member;

(b) a first pressure detecting mechanism disposed at a first portion of the body member;

(c) a second pressure detecting mechanism disposed at a second portion of the body member, the second pressure detecting mechanism being spaced apart from the first pressure detecting mechanism along a length of the body member; and (d) an attaching mechanism that releaseably secures the body member to a second catheter, wherein the attaching mechanism includes defining a cavity within the body member, the cavity being sized and structured such that the second catheter is adapted to be selectively secured within the cavity.

\* \* \* \* \*